United States Patent
Rinner

(10) Patent No.: US 6,575,042 B1
(45) Date of Patent: Jun. 10, 2003

(54) BEAM-TYPE TORSION APPLYING AND MEASURING TOOL

(75) Inventor: James A. Rinner, Racine, WI (US)

(73) Assignee: Beere Precision Medical Instruments, Inc., Kenosha, WI (US)

( * ) Notice: Subject to any disclaimer, the term of this patent is extended or adjusted under 35 U.S.C. 154(b) by 0 days.

(21) Appl. No.: 10/074,426

(22) Filed: Feb. 13, 2002

(51) Int. Cl.[7] .............................. G01N 3/22; G01N 3/26
(52) U.S. Cl. .................. 73/847; 73/847; 73/862.21; 73/862.22; 73/862.29; 73/862.32; 81/478; 81/477; 81/47; 192/56.1; 604/164; 604/280; 16/198; 399/12; 134/279
(58) Field of Search ................................ 73/847, 862.21, 73/862.23, 862.29, 862.22, 862.333; 81/478, 477, 467; 192/56.1; 604/164, 280; 16/198; 399/12; 434/279; 340/665; 273/186 A; 177/196

(56) References Cited

U.S. PATENT DOCUMENTS

| | | | |
|---|---|---|---|
| 2,394,022 A | 2/1946 | Storrie |
| 2,417,402 A | 3/1947 | Storrie |
| 2,464,372 A | 3/1949 | Booth |
| 2,934,946 A | 5/1960 | Engquist |
| 4,359,906 A | 11/1982 | Cordey |
| 4,558,601 A | 12/1985 | Stasiek et al. |
| 5,048,381 A | 9/1991 | Allen et al. |
| 5,762,629 A | 6/1998 | Kambin |

*Primary Examiner*—Max Noori
*Assistant Examiner*—Octavia Davis
(74) *Attorney, Agent, or Firm*—Arthur J. Hansmann

(57) ABSTRACT

A beam-type torquing and measuring tool having two telescoping members rotationally attached together at a first end of each, and they are relatively rotatable at the other end. One member transmits torque to the workpiece and has a pointer thereon, and the other member has a scale readable relative to the pointer to measure the torque being applied. The members have a central opening extending axially therethrough for canalization, and there may be adapters threadedly attached to the tool ends, and the scale and pointer can be read in their two diametrically opposite locations.

20 Claims, 2 Drawing Sheets

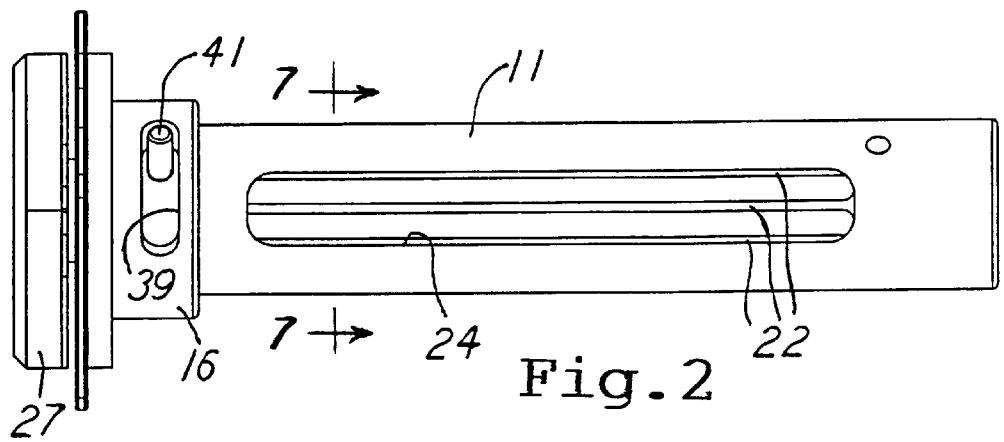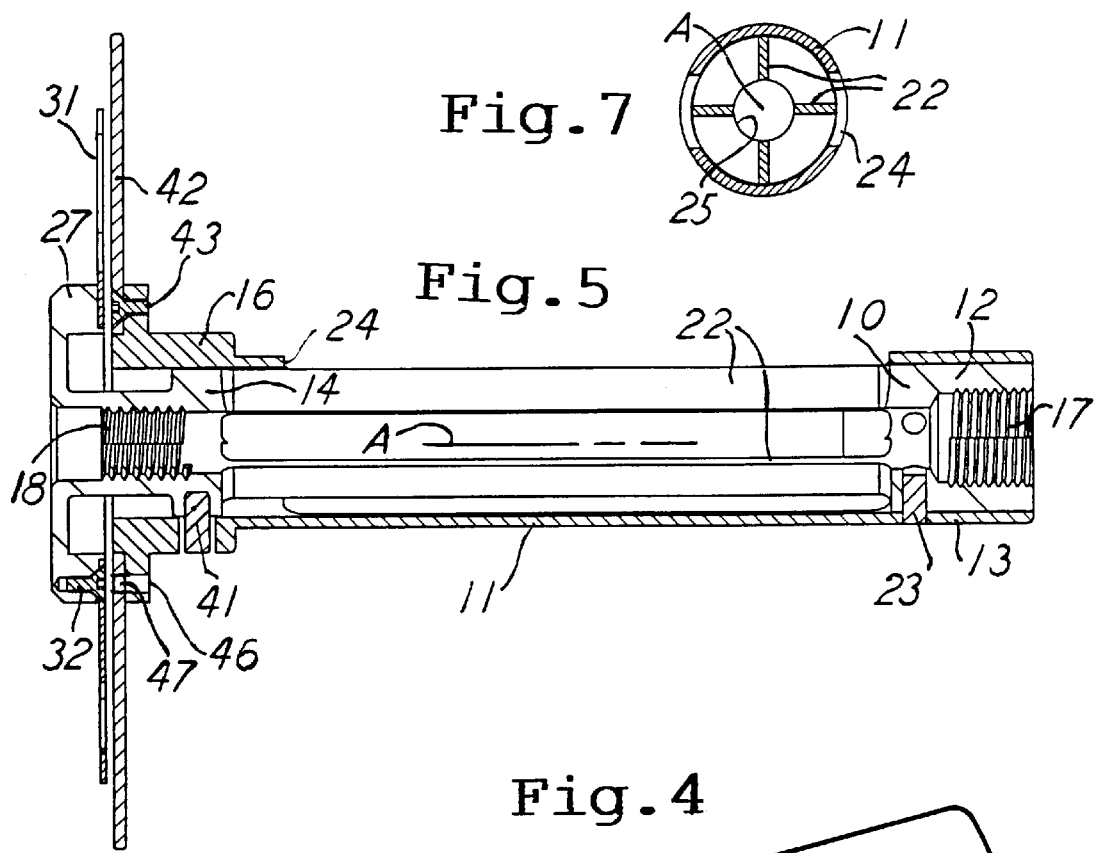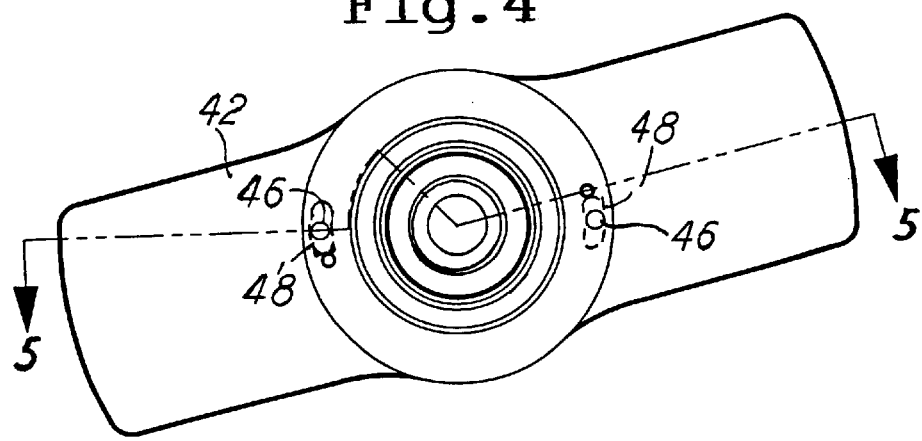

BEAM-TYPE TORSION APPLYING AND MEASURING TOOL

This invention relates to a beam-type torsion applying and measuring tool. It is particularly useful in the medical field, such as in the securing of a threaded fastener in a patient's body.

BACKGROUND OF THE INVENTION

The prior art is aware of various tools for applying threaded fasteners into a patient's body in the practice of the medical arts. Also, the prior art is aware of tools that apply a torque to a threaded fastener and simultaneously display the amount of torque that is being applied. Still further, there are tools that employ springs which extend between a handle and a fastener driver on the tool, all for applying and measuring torque.

The present invention improves upon the prior art in that it has torsion beams between a handle and a fastener driver wherein the beams are radially offset from the longitudinal axis of the tool to thereby present a central clearance through the tool for canalization functions. In one embodiment of this invention, there are more than two such beams extending longitudinally of the tool, and the beams can individually twist for applying the torque.

Still further, the present invention has threaded ends for the reception of adapters which are effective in the performance of work accomplished in the use of the tool.

Additionally, the present invention has a scale and pointer indicator for indicating the amount of torque being applied, and the indicator is selectively adjustable for calibration. Also, the indicator extends to the two diametrically opposite sides of the tool so it can be read in those two positions and therefore is always visible to the operator and is not covered by the operator's hand.

There is a light weight but sturdy tool which is susceptible to precision handling for performing its functions and which is sensitive to accurately measuring the torque being applied by the torsion imposed through the tool.

BRIEF DESCRIPTION OF THE DRAWINGS

FIG. 2 is a bottom plan view of FIG. 1.

FIG. 4 is a right end elevational view of FIG. 2.

FIG. 5 is a sectional view taken along the irregular line designated 5—5 on FIG. 4.

FIG. 7 is a sectional view taken along the line designated 7—7 on FIG. 2.

DETAILED DESCRIPTION OF A PREFERRED EMBODIMENT

Figure 1:
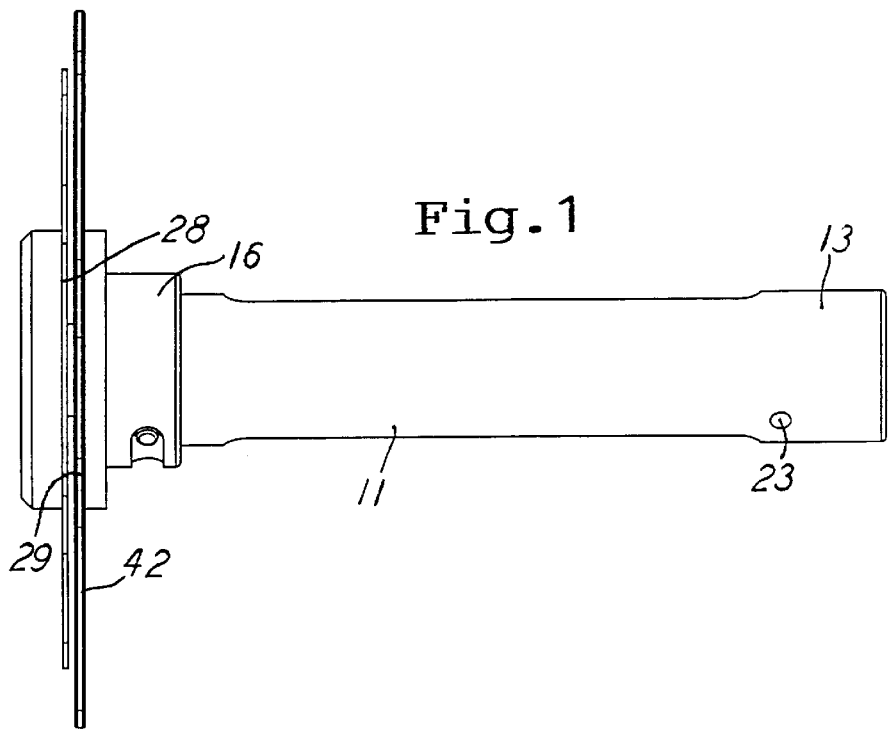
FIG. 1 is a side elevational view of a preferred embodiment of the tool of this invention.
Figure 3:
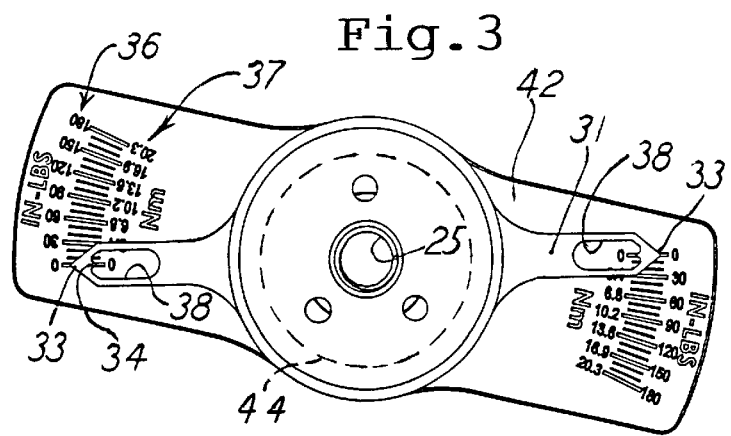
FIG. 3 is a left end elevational view of FIG. 2.

The tool of this invention includes two telescopic members 10 and 11 which are generally cylindrical and extend along a central and longitudinal axis designated A, and as seen in FIG. 5. The members 10 and 11 have respective first ends 12 and 13 and respective seconds ends 14 and 16. Those longitudinally spaced apart ends 12 and 14 of member 10 are shown to be circular and are disposed on the interior of the circular ends 13 and 16 of the member 11.

Figure 6:
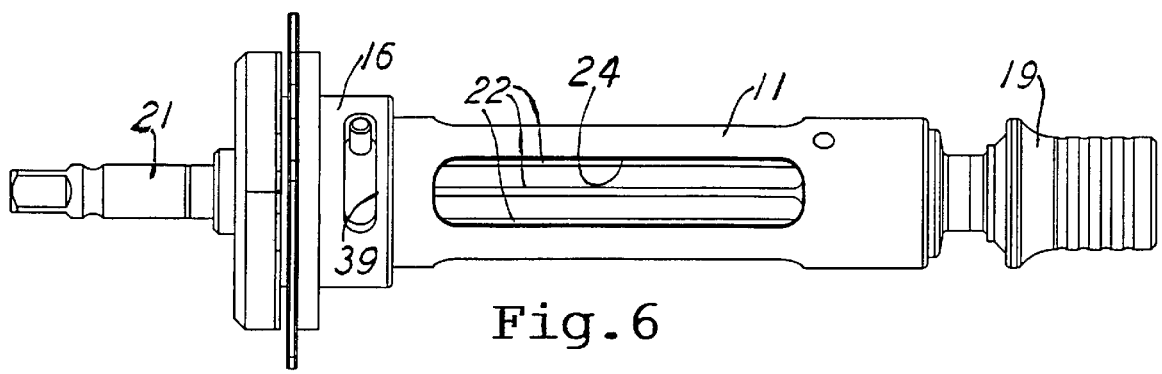
FIG. 6 is a side elevational view similar to FIG. 2 but of another embodiment of the tool, and with two parts added thereto at the opposite ends thereof.

The ends 12 and 14 are shown to respectively have screw threads 17 and 18, and those threaded openings can receive adapters or the like such as the shown parts 19 and 21 seen in FIG. 6. Thus, an unshown threaded fastener engager can be attached at the end 12 and an unshown operator's handle can be attached at the end 14. The adapters 19 and 21 represent those attachable parts which the operator can select and attached to the tool, as shown.

In that arrangement, the member 10 can be employed to transmit a torque between its ends 14 and 12 and that torque can be applied to an unshown threaded fastener work piece, such as a screw in a patient's bone structure. To transmit that torque through the member 10, there are four torsion beams 22 extending on and along the length of member 10 between its ends 12 and 14. The beams 22 are spaced from the axis A, and they are thin in cross sectional shape, such as shown in FIGS. 2, 6, and 7, to thus be sensitive to the amount of torque being applied in the rotational direction in line with the narrow thickness and throughout the lengths of the beams. Thus, the thickness of the beams 22 is less than the extent of the beams in their radial height direction, as seen in FIG. 7, thus the beams are sensitive in responding to the torque imposed upon them and in registering that torque. That thickness is in the tangential direction about axis A, and the height is in the radial direction relative to axis A.

Being spaced apart, both circularly and radially, the beams leave a central and axial extending opening 25 extending completely through the tool, and thus the arrangement is for canalization functions of the usual nature performed with medical tools, such as receiving a rod along axis A for extending through the tool and be present to engage an unshown threaded fastener or the like at the end of the tool.

The members 10 and 11 are connected together at their first ends 12 and 13 by means of a pin 23 which radially extends into those ends 12 and 13. Accordingly, the ends 12 and 13 always rotate in unison about the axis A. The member 11 has two diametrically opposite slots or openings 24 shown in FIG. 2, and, as seen in FIG. 6, there are four such slots. The provision of two or four slots 24 reduces the weight of the tool and exposes the interior thereof for observation.

The second ends 14 and 16 of the members 10 and 11 are free to rotate about axis A relative to each other, and the circular surfaces at 26, which are respectively on the members 10 and 11, are rotational bearing surfaces.

The end 14 has the screw threads 18 to which a handle can be attached for the rotation. Also, the end 14 presents a hub 27 with a circularly extending planar surface 28. The end 14 has a circularly extending planar surface 29. A double arrow head pointer 31 is on the surface 28 and is attached thereto by screws, such as the shown screw 32. The pointer 31 thus rotates with the rotation of the member 10 which is the driver for the unshown threaded fastener or work piece. Also, the pointer, at its two pointing ends, has two arrows 33 and 34 so that the location of the two arrows can be seen respectively pointing radially outwardly and radially inwardly. Each arrow 33 aligns with a measuring scale 36 showing inch/pounds, and each arrow 34 aligns with a measuring scale 37 showing metric readings. Openings 38 in the pointer permits the operator to read the measurement on both scales 37. The arrows 33 and 34 are positioned radially from axis A to extend beyond the operator's hand when he is gripping an unshown handle which could be on the axis A, and that is a distance of a couple inches, and he can read either one of the two indicators, whichever one is most readable at the moment of the operating position.

The markings on the scales 36 and 37 are of small sizes to permit reading the numbers through the larger openings 38 so the operator definitely knows what numerical position the pointers are at.

The ends 14 and 16 relate in a lost motion relationship such that end 14 can rotate without rotation of the end 16. Thus there is a circumferential slot 39 in end 16 and there is a pin 41 in the end 14, and the pin 41 extends into the slot 39. Upon the application of rotating torque on the member 10, and assuming the members 10 and 11 are already fully engaged with the unshown fastener and there being little or no rotation continuing, member 10 will twist through beams 22 about axis A while member 11 will remain fixed and not rotate. Thus, a scale plate 42, which displays the scales 36 and 37, will remain fixed. When the pointer moves, it will show the amount of the torque being applied.

So the scale plate 42 is attached to the end 16 through screws, such as screw 43, which hold the scale plate 42 against the planar surface 29. The two pointers 31 are joined together by having a circular portion 44 which is rotatably piloted on the hub 27 for rotation about axis A and relative to the hub 27. The portion 44 can be held against the surface 28 by the screws 32. The end 16 and the plate 42 have openings, such as the shown respective openings 46 and 47, which align with the screws 32 on the hub 27. A screw driver can pass through the openings 46 and 47 to loosen and tighten the screws 32 and thereby permit rotational adjustment of the pointers 31 in the calibration thereof. Slots 48 in the pointer portion 44 allow for the rotational adjustment of the pointers 31 relative to the scales 36 and 37. Thus the pointers 31 can be rotationally adjustably positioned and thereby be calibrated relative to the scale plate 42.

With the lost motion of the slot 39 and pin 41, the members 10 and 11 can not be over stressed because of overturning the member 10 relative to the member 11 which will receive the rotation torque when the pin 41 travels to the lower end of the slot 39. Also, with the employment of the pin 23, no welding or the like is required for joining the members 10 and 11 together at their first ends.

The concept is that of a sturdy but light weight touring and measuring tool with a canalization feature, touring beams which are thin in cross section, double pointers, a calibratable scale, and the other features inherent in the foregoing description.

What is claimed is:

1. A beam-type torsion applying and measuring tool comprising:

a first and a second cylindrical member with each thereof having first and second ends and a length extending between said ends and having a central axis along said length and a hollow interior along said axis and extending completely through said members, said first ends being connected together for identical rotation together about said axis, said first end of said first member having a portion for engaging a fastener of a threaded type, said first member having resilient torsion-responsive beams extending between its said ends and being radially spaced from said axis for rotation about said axis of said second one of its said ends relative to said first one of its said ends upon torsional twisting of said first member, and a pointer and a scale respectively separately attached with said first and said second members at said second ends thereof, whereby rotation of said second end of said first member about said axis relatively rotates said pointer and said scale whereby said pointer indicates relative to said scale the amount of relative rotation between said members and thereby indicates the amount of torque being applied to the fastener.

2. The beam-type torsion applying and measuring tool as claimed in claim 1, wherein:

said beams are at least three in number and are equally circumferentially spaced around said first member.

3. The beam-type torsion applying and measuring tool as claimed in claim 1, wherein:

said beams are four in number and are equally circumferentially spaced around said first member.

4. The beam-type torsion applying and measuring tool as claimed in claim 1, including:

one of said pointer and said scale being rotatable about said axis and its respective said member for selective adjustable positioning on said its said member, and a fastener releasable engaged between said one of said pointer and said scale for the attachment thereof in the adjusted position.

5. The beam-type torsion applying and measuring tool as claimed in claim 1, including:

a limited lost motion connector connected between said second ends of said members and providing limited relative rotation on said first member relative to said second member.

6. The beam-type torsion applying and measuring tool as claimed in claim 5, wherein:

said connector is a pin and slot respectively on said members and with said slot extending partly around said axis and with said pin disposed in said slot.

7. The beam-type torsion applying and measuring tool as claimed in claim 1, wherein:

said scale and said pointer both are in pairs and extend to two diametrically opposite sides of said axis to thereby be visible at either of the sides.

8. The beam-type torsion applying and measuring tool as claimed in claim 1, including:

said first ends of said members having an adapter receiving portion and said second end of said first member having a handle receiving portion for rotating said first member.

9. A beam-type torsion applying and measuring tool comprising:

a first and a second cylindrical member with each thereof having first and second ends and a length extending between said ends and having a central axis along said length, said first ends being connected together for identical rotation together about said axis, said first end of said first member having a portion for engaging a fastener of a threaded type, said first member having resilient torsion-responsive beams extending between its said ends and being radially spaced from said axis for rotation about said axis of said second one of its said ends relative to said first one of its said ends upon torsional twisting of said first member, a pointer and a scale respectively separately attached with said first and said second members at said second ends thereof, whereby rotation of said second end of said first member about said axis relatively rotates said pointer and said scale whereby said pointer indicates relative to said scale the amount of relative rotation between said members and thereby indicates the amount of torque being applied to the fastener, and said ends of said first member being threaded for respectively threaded receiving adapters connectable to said first member.

10. The beam-type torsion applying and measuring tool as claimed in claim 9, wherein:

said beams are at least three in number and are equally circumferentially spaced around said first member.

11. The beam-type torsion applying and measuring tool as claimed in claim 9, wherein:

said beams are four in number and are equally circumferentially spaced around said first member.

12. The beam-type torsion applying and measuring tool as claimed in claim 9, including:

one of said pointer and said scale being rotatable about said axis and its respective said member for adjustable positioning on said its said member, and a fastener releasable engaged between said one of said pointer and said scale for the attachment thereof in the adjusted position.

13. The beam-type torsion applying and measuring tool as claimed in claim 9, including:

a limited lost motion connector connected between said second ends of said members and providing limited relative rotation on said first member relative to said second member.

14. The beam-type torsion applying and measuring tool as claimed in claim 13, wherein:

said connector is a pin and slot respectively on said members and with said slot extending partly around said axis and with said pin disposed in said slot.

15. The beam-type torsion applying and measuring tool as claimed in claim 9, wherein:

said scale and said pointer both are in pairs and extend to two diametrically opposite sides of said axis to thereby be visible at either of the sides.

16. The beam-type torsion applying and measuring tool as claimed in claim 9, including:

said first ends of said members having an adapter receiving portion and said second end of said first member having a handle receiving portion for rotating said first member.

17. The beam-type torsion applying and measuring tool as claimed in claim 9, wherein:

said beams are radially spaced from said axis and said members thereby have a hollow longitudinal center along said axis.

18. A beam-type torsion applying and measuring tool comprising:

a first and a second cylindrical member with each thereof having first and second ends and a length extending between said ends and having a central axis along said length, said first ends being connected together for identical rotation together about said axis, said first end of said first member having a portion for engaging a fastener of a threaded type, said first member having resilient torsion-responsive beams extending between its said ends and being radially spaced from said axis for rotation about said axis of said second one of its said ends relative to said first one of its said ends upon torsional twisting of said first member, a pointer and a scale respectively separately attached with said first and said second members at said second ends thereof, whereby rotation of said second end of said first member about said axis relatively rotates said pointer and said scale whereby said pointer indicates relative to said scale the amount of relative rotation between said members and thereby indicates the amount of torque being applied to the fastener, and said beams having two cross-sectional dimensions extending transverse to said length and with one of the dimensions extending in the direction of rotation and the other of the dimensions extending radially of said axis and with the one dimension being smaller then the other dimension for twisting of said beams in response to torque applied thereto.

19. The beam-type torsion applying and measuring tool as claimed in claim 18, wherein:

said beams are at least three in number and are equally spaced from said axis and circumferentially spaced around said first member.

20. The beam-type torsion applying and measuring tool as claimed in claim 18, wherein:

said beams are four in total number and are equally spaced from said axis and circumferentially spaced around said first member.

\* \* \* \* \*